(12) United States Patent
Pereira et al.

(10) Patent No.: US 10,542,969 B2
(45) Date of Patent: Jan. 28, 2020

(54) KNOTTING DEVICE AND METHODS OF USING THE SAME

(71) Applicant: Boston Scientific Scimed, Inc., Maple Grove, MN (US)

(72) Inventors: Peter J. Pereira, Mendon, MA (US); Aaron Campbell, Grafton, MA (US); Joseph Gordon, Mansfield, MA (US); William J. Kane, Sutton, MA (US); Shane Siwinski, Providence, RI (US); Ayan A. Bhandari, Roanoke, VA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 15/270,584

(22) Filed: Sep. 20, 2016

(65) Prior Publication Data

US 2017/0079638 A1 Mar. 23, 2017

Related U.S. Application Data

(60) Provisional application No. 62/221,303, filed on Sep. 21, 2015.

(51) Int. Cl.
*A61B 17/04* (2006.01)

(52) U.S. Cl.
CPC ...... *A61B 17/0469* (2013.01); *A61B 17/0485* (2013.01)

(58) Field of Classification Search
CPC . A61B 17/0401; A61B 17/0487; A61B 17/04; A61B 17/0482; A61B 17/0485; A61B 17/0493; A61B 17/0495; A61B 17/06119; A61B 17/06128; A61B 2017/0495; A61B 2017/0496
USPC .................................................. 606/148, 232
See application file for complete search history.

(56) References Cited

U.S. PATENT DOCUMENTS

| | | | | |
|---|---|---|---|---|
| 5,391,176 A | * | 2/1995 | de la Torre | A61B 17/0469 606/139 |
| 5,472,446 A | * | 12/1995 | de la Torre | A61B 17/0469 289/17 |
| 5,797,928 A | * | 8/1998 | Kogasaka | A61B 17/0469 606/139 |
| 8,323,316 B2 | * | 12/2012 | Maiorino | A61B 17/0401 606/228 |

* cited by examiner

*Primary Examiner* — Melanie R Tyson
(74) *Attorney, Agent, or Firm* — Brake Hughes Bellermann LLP

(57) ABSTRACT

According to an aspect, a device includes an elongate member, a suture, and a needle. The elongate member has a first end portion and a second end portion. The elongate member defines a lumen and a slot. The lumen extends from the first end portion to the second end portion. The slot extends from the first end portion to the second end portion. A portion of the suture is wrapped around the elongate member. The needle is coupled to the suture.

19 Claims, 9 Drawing Sheets

KNOTTING DEVICE AND METHODS OF USING THE SAME

CROSS-REFERENCE TO RELATED APPLICATION

This application is a Nonprovisional of, and claims priority to, U.S. Patent Application No. 62/221,303, filed on Sep. 21, 2015, entitled "KNOTTING DEVICE AND METHODS OF USING THE SAME", which is incorporated by reference herein in its entirety.

TECHNICAL FIELD

This disclosure relates generally to medical devices and more particularly to medical devices that are configured to be used to facilitate the coupling of bodily implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient and coupled or attached to various locations within the body using a series of sutures or knots. For example, in procedures such as sacrocolpopexy procedures, a suture may be tied 4 to 8 times to form a single knot and a series of 12 or 14 or more knots may be used to secure an implant within the body of the patient. Accordingly, a procedure for placing and attaching an implant within a body of a patient may require time and skill.

Accordingly, it may be desirable to provide device or tool that facilitates the coupling or attaching of a bodily implant within a body of a patient. Specifically, it may be desirable to provide a device or tool that facilitates the tying of knots to secure the implant in place within the body of the patient.

SUMMARY

According to an aspect, a device includes an elongate member, a suture, and a needle. The elongate member has a first end portion and a second end portion. The elongate member defines a lumen and a slot. The lumen extends from the first end portion to the second end portion. The slot extends from the first end portion to the second end portion. A portion of the suture is wrapped around the elongate member. The needle is coupled to the suture.

In some embodiments, the portion of the suture is wrapped around the elongate member a plurality of times. In some embodiments, the elongate member defines a groove, the groove being configured to receive the needle. In some embodiments, the elongate member includes a coupling portion, the coupling portion being configured to removably couple the needle to the elongate member.

In some embodiments, the first end portion of the elongate member has a first size, the second end portion of the elongate member has a second size, the first size being greater than the second size. In some embodiments, the elongate member includes a tapered portion.

In some embodiments, the device includes a support member, the support member being coupled to the elongate member and extending around at least a portion of the elongate member and the portion of the suture that is wrapped around the elongate member. In some embodiments, the device includes a support member, the support member having a "C"-shaped cross-section, the support member being coupled to the elongate member and extending around at least a portion of the elongate member and the portion of the suture that is wrapped around the elongate member. In some embodiments, the device includes an extension member coupled to and extending from the elongate member. In some embodiments, the device includes an extension member coupled to and extending from the elongate member, the extension member having a loop portion.

In some embodiments, a first end portion of the support member has a first size, a second end portion of the support member has a second size, the first size being greater than the second size. In some embodiments, the support member includes a tapered portion. In some embodiments, the support member defines a slot and a cavity in fluid communication with the slot, the slot being configured to receive the needle.

In some embodiments, the elongate member includes a sidewall. In some embodiments, the elongate member includes a sidewall having a "C"-shaped cross-section.

In some embodiments, the the support member defines a cavity and a slot in communication with the cavity, the slot being configured to receive the needle and the cavity being configured to house the needle.

In some embodiments, a device includes an elongate member, the elongate member having sidewall and having a first end portion and a second end portion, the sidewall of the elongate member having a substantially C-shaped cross-section; a suture, a portion of the suture being wrapped around the elongate member; and a needle, the needle being coupled to the suture.

In some embodiments, the portion of the suture is wrapped around the elongate member a plurality of times.

In some embodiments, the device includes a support member, the support member being coupled to the elongate member and extending around at least a portion of the elongate member and the portion of the suture that is wrapped around the elongate member.

In some embodiments, the support member defines a cavity, the cavity being configured to receive the needle.

In some embodiments, the device includes an extension member coupled to and extending from the elongate member.

In some embodiments, a method includes inserting a medical device into a body of a patient, the medical device including an elongate member, a suture being wrapped around at least a portion of the elongate member, and a needle coupled to the suture; passing the needle through bodily tissue; passing the needle through a lumen defined by the elongate member; and pulling on a first end portion of the suture and a second end portion of the suture to form a knot in the suture.

In some embodiments, the method includes removing the portion of the suture that is wound around the elongate member from the elongate member. In some embodiments, the method includes passing the needle through a bodily implant before the passing the needle through a lumen defined by the elongate member.

In some embodiments, the inserting the medical device into the body of the patient includes passing the medical device through a trocar.

In some embodiments, the method includes removing the needle from the body of the patient.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
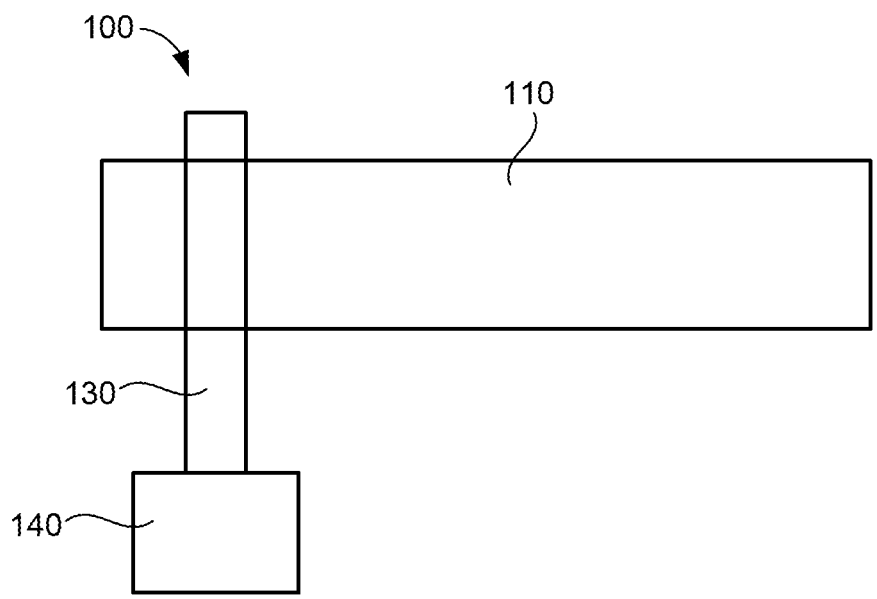
FIG. 1 is a schematic illustration of a medical device according to an embodiment.

FIG. 1 is a schematic illustration of a medical device 100 according to an embodiment of the invention. The medical device 100 may be used to couple or attach a bodily implant (or implant) within a body of a patient. For example, the medical device 100 may be used to couple or attach an implant within a pelvic region of a patient. For example, in some embodiments, the medical device 100 may be used in a sacrocolpopexy procedure to couple an implant to a vagina or tissue proximate a vagina of a patient. In other embodiments, the medical device 100 may be used to couple or attach different types of bodily implants into different locations within the body of the patient. In some embodiments, the medical device 100 may be used to couple one portion of bodily tissue to another portion of bodily tissue.

The medical device 100 includes an elongate member 110, a suture 130, and a needle 140. The elongate member 110 has a first end portion and second end portion. In some embodiments, the elongate member 110 defines a lumen that extends from the first end portion to the second end portion. In some embodiments, the elongate member also defines a slot that extends from the first end portion to the second end portion. In some embodiments, the slot is in fluid communication with the lumen. In other words, the slot is disposed adjacent to or leads to the lumen.

The elongate member 110 can be of any shape or size. In some embodiments, the elongate member is tubular with an outer surface that is generally smooth and round. In other embodiments, the elongate member 110 has a different shape. In some embodiments, the elongate member 110 is about as long as the length of the windings of the suture 130. In other embodiments, the elongate member 110 has a length that is slightly greater than the length of the windings of the suture 130.

The suture 130 is configured to be tied to a bodily implant and bodily tissue to help secure the bodily implant within the body of the patient. The suture 130 can be formed or any type of biocompatible material. In some embodiments, the suture 130 is wrapped or wound around the elongate member 110 (such as the outer surface of the elongate member 110). In other words, in some embodiments, the suture 130 extends around, traverses, or is otherwise disposed adjacent the outer surface of the elongate member 110. In some embodiments, the suture 130 is wrapped or wound around the elongate member 110 a single time. In other embodiments, the suture 130 is wrapped or wound around the elongate member 110 a more than once or a plurality of times. In some embodiments, the suture 130 is wrapped or wound around the elongate member 110 between 5 and 15 times. In some embodiments, the suture 130 is wrapped or wound around the elongate member 110 in linearly (the winds or loops of the suture 130 are substantially parallel with each other). In other embodiments, the suture 130 is wrapped or wound around the elongate member 110 such that the suture 130 is crisscrossed (or the winds or loops of the suture 130 is twisted). In other embodiments, the suture 130 is wrapped or wound around the elongate member 110 such that the suture 130 is wrapped on itself (the winds or loops of the suture 130 are on top of each other). In some embodiments, the suture 130 is wrapped or wound around the elongate member 110 in one direction. In other embodiments, the suture 130 is wrapped or wound around the elongate member 110 in two directions (a first direction and a second opposite direction).

In some embodiments, a single suture is wrapped or wound around the elongate member 110. In other embodiments, more than one suture is wrapped or wound around the elongate member 110. For example, in some embodiments, between 3 and 10 sutures are wrapped or wound around the elongate member 110. In some embodiments, more than 10 sutures are wrapped or wound around the elongate member 110.

In some embodiments, the device 100 includes a rod or linear member disposed within the slot defined by the elongate member. The rod or linear member may function to keep the loops of the suture aligned with each other.

The needle 140 is coupled to an end portion of the suture 130. The needle 140 is configured to pierce bodily tissue and guide the suture 130 or a portion of the suture 130 through bodily tissue and/or a bodily implant. In some embodiments, the needle or needle member 140 includes a sharp or tissue piercing end portion.

In use, the medical device 100 may be used to secure or help secure a bodily implant within a body of a patient. For example, in some embodiments, the medical device 100 may be used to knot or tie suture knots to help secure the implant within the body of the patient.

In some embodiments, the medical device 100 may be inserted into a body of a patient. For example, in some embodiments, the medical device 100 is sized and shaped to be inserted into a body of a patient via a trocar. Specifically, in some embodiments, the medical device 100 is sized and shaped to be inserted into the body of the patient via a 10 mm-12 mm trocar. In other embodiments, the medical device 100 is sized and shaped to be inserted into the body via trocar that is smaller than 10 mm.

In some embodiments, the medical device 100 may be disposed adjacent a bodily implant that has been placed or inserted into the body. The needle 140 may be used to pass a portion of the suture 130 through the implant and through bodily tissue. For example, the needle 140 may be pressed or pushed against the implant and the bodily tissue to thread the suture 130 through the implant and through the bodily tissue.

The needle 140 may then be passed through the windings of the suture 130. For example, in some embodiments, the needle 140 and a portion of the suture 130 may be passed through the lumen defined by the elongate member 110 to extend or pass the needle 140 and a portion of the suture 130 through the windings of the suture (the portion of the suture 130 that is wound or wrapped around the elongate member 110).

The suture 130 may then be removed from the elongate member 110. For example, the suture 130 or the portion of the suture 130 that is wound around the elongate member 110 may be slid off of the elongate member to remove the suture from the elongate member 110. The end portions of the suture 130 (one end portion that is coupled to the needle 140 and the opposite end portion) may then be pulled to cinch or secure the knot against the implant and the bodily tissue.

In some embodiments, then needle 140 may then be cut from the suture 130 to free the needle 140 from the suture 130. The elongate member 110 and the needle 140 may then be removed from the body of the patient. In some embodiments, the needle 140 may be coupled to the elongate member 110 and the needle and the elongate member may be removed from the body of the patient together.

In some embodiments, a housing or support member houses or retains more than one elongate member 110. Each elongate member 110 may have a single suture wrapped or wound around the elongate member 110. In some embodiments, each elongate member 110 may be removed from the housing or support member one at a time from an end of the housing or support member. In some embodiments, the housing or support member includes an advancement member, such as a spring or other biasing member, that is configured to advance the remaining elongate members within the housing or support member when one of the elongate members is removed.

Figure 2:
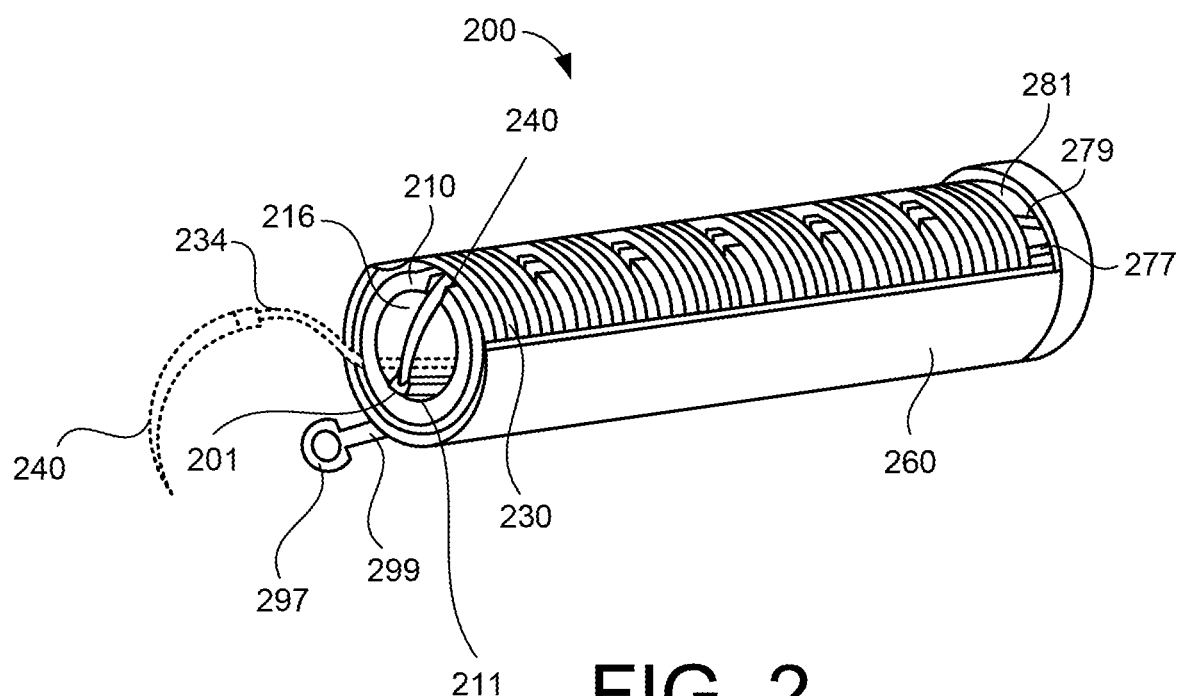
FIG. 2 is a perspective view of a medical device according to an embodiment.
Figure 3:
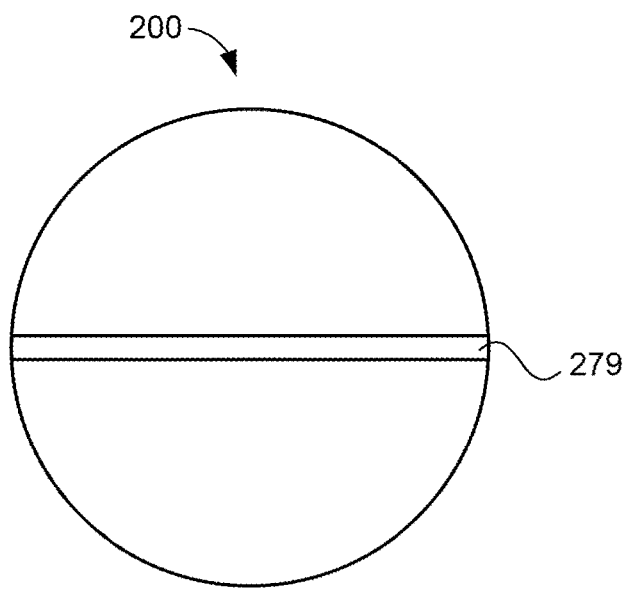
FIG. 3 is an end view of the medical device of FIG. 2.
Figure 4:
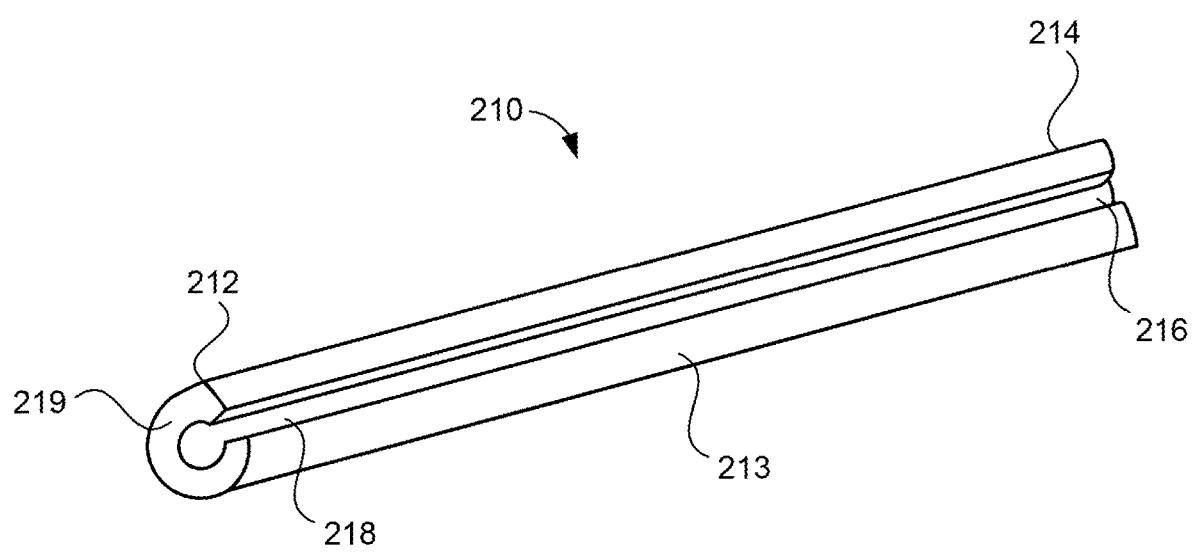
FIG. 4 is a perspective view of an elongate member of the medical device of FIG. 2.
Figure 5:
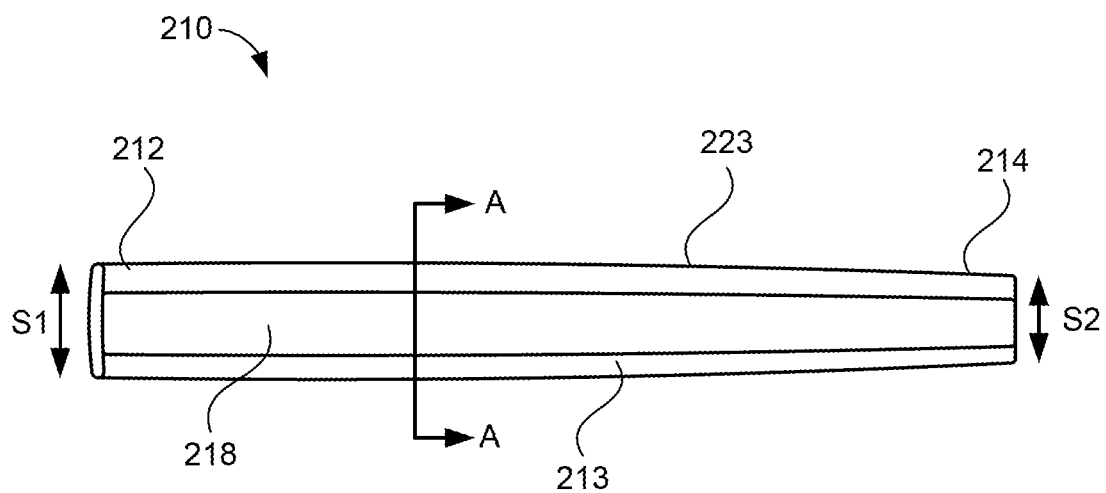
FIG. 5 is a side view of the elongate member of FIG. 4.
Figure 6:
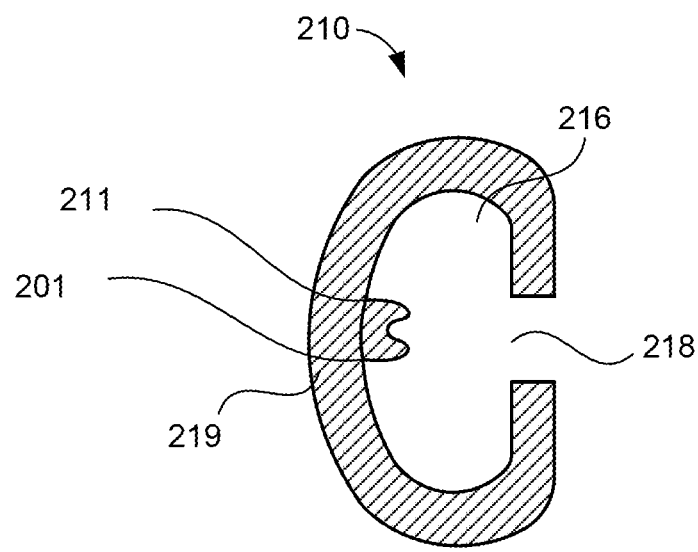
FIG. 6 is a cross-sectional view of the elongate member taken along line A-A of FIG. 5.
Figure 7:
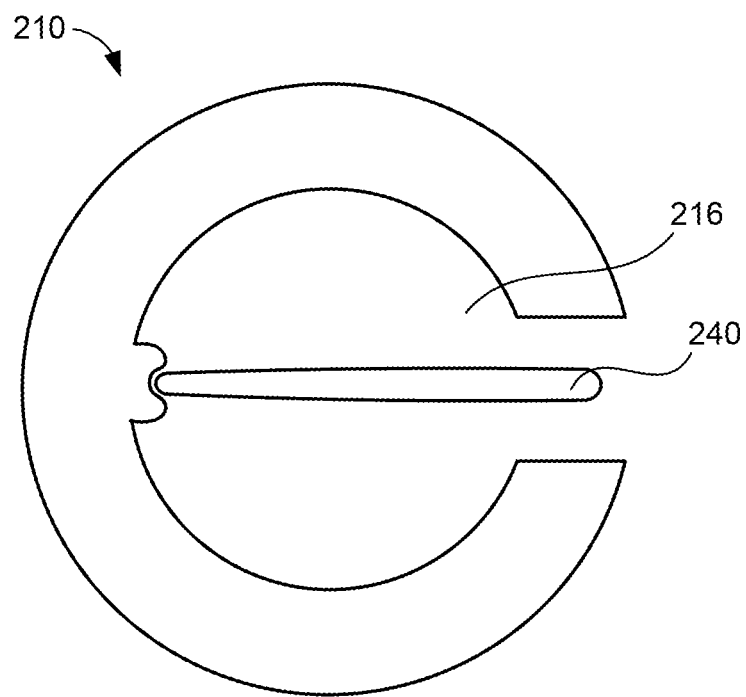
FIG. 7 is an end view of the elongate member of FIG. 4.
Figure 8:
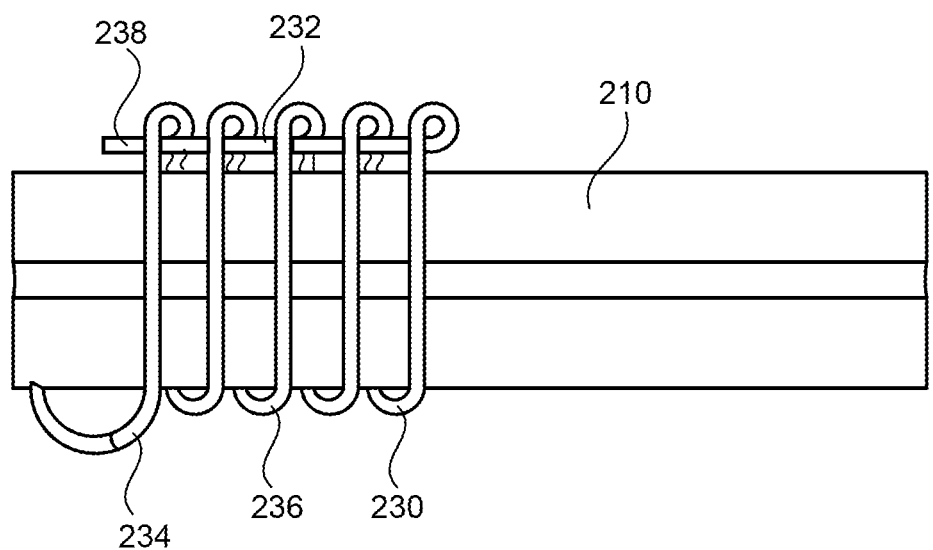
FIG. 8 is a side view of the elongate member of FIG. 4 with a suture wrapped around it.
Figure 9:
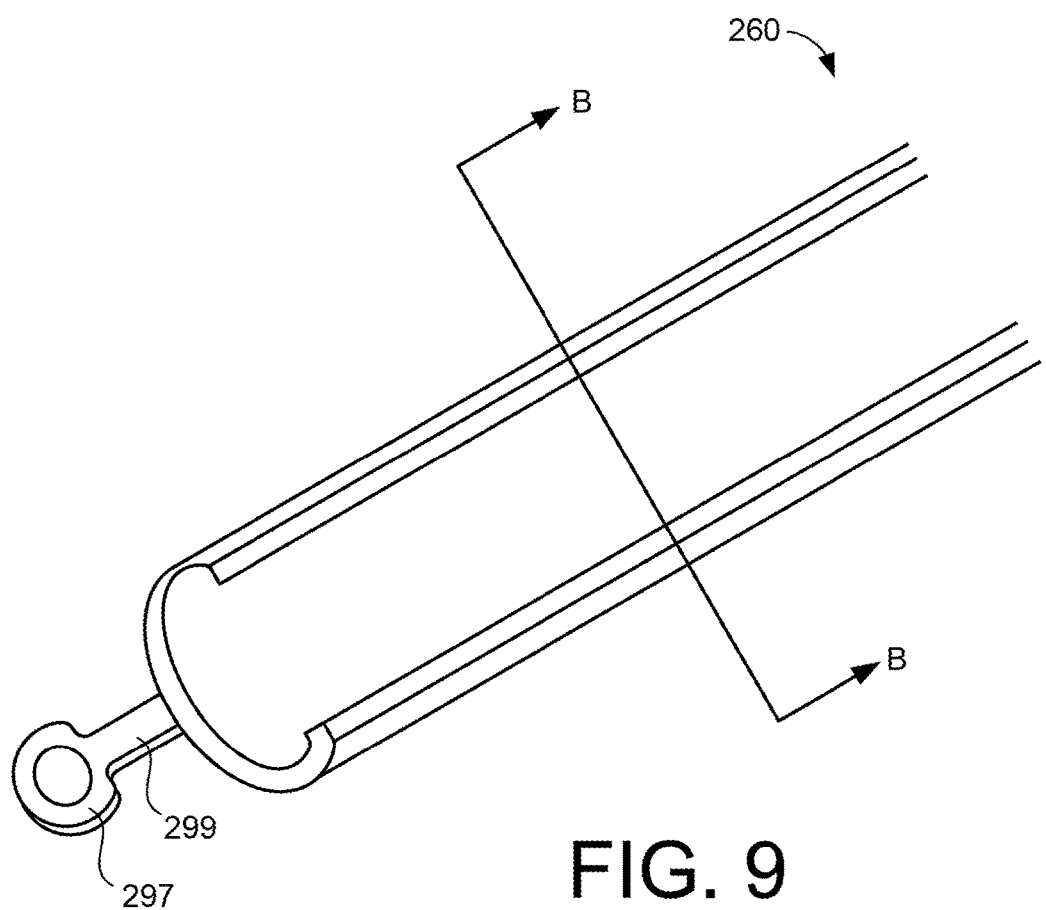
FIG. 9 is a perspective view of a support member of the medical device of FIG. 2.
Figure 10:
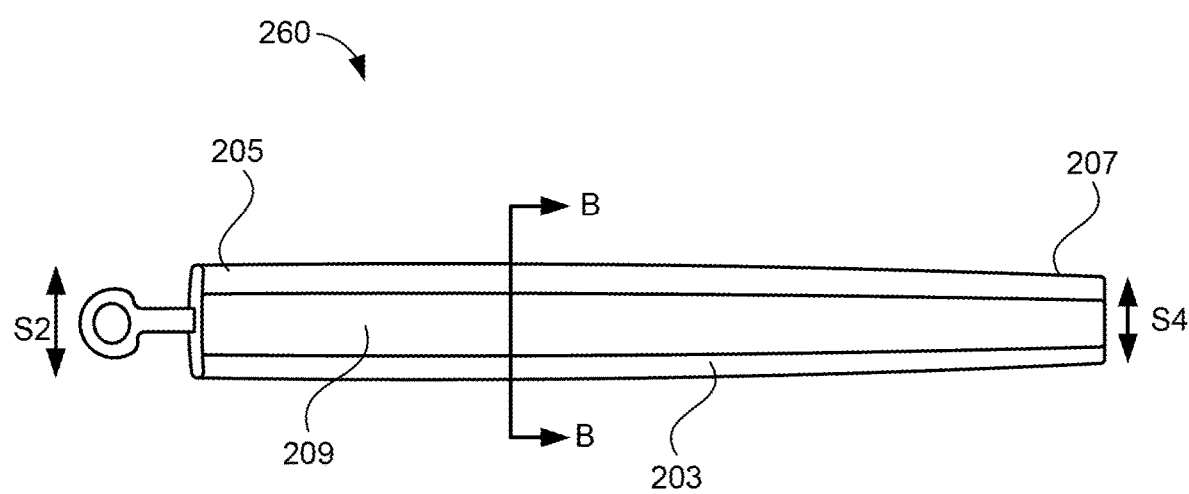
FIG. 10 is a side view of the support member of FIG. 9.
Figure 11:
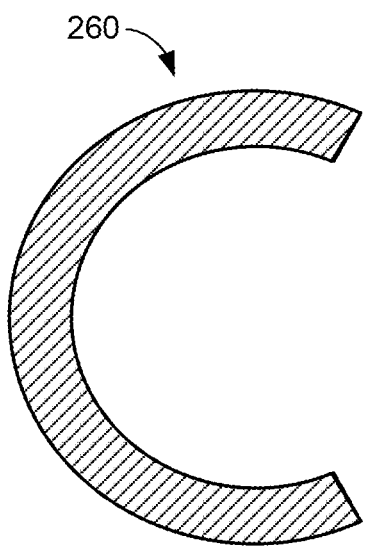
FIG. 11 is a cross-sectional view of the support member of FIG. 9 taken along line B-B of FIG. 9.

FIG. 2 is a perspective view of a medical device 200 according to an embodiment. FIG. 3 is an end view of the medical device 200. FIG. 4 is a perspective view of an elongate member 210 of the medical device 200. FIG. 5 is a side view of the elongate member 210. FIG. 6 is a cross-sectional view of the elongate member 210 taken along line A-A of FIG. 5. FIG. 7 is an end view of the elongate member 210. FIG. 8 is a side view of the elongate member 210 with a suture 230 wrapped around it. FIG. 9 is a perspective view of a support member 260 of the medical device 200. FIG. 10 is a side view of the support member 260. FIG. 11 is a cross-sectional view of the support member 260 taken along line B-B of FIG. 10.

The medical device 200 may be used to couple or attach a bodily implant within a body of a patient. For example, the medical device 200 may be used to couple or attach a bodily implant within a pelvic region of a patient. For example, in some embodiments, the medical device 200 may be used in a sacrocolpopexy procedure to couple a bodily implant to a vagina or tissue proximate a vagina of a patient. In other embodiments, the medical device 200 may be used to couple or attach different types of bodily implants into different locations within the body of the patient. In some embodiments, the medical device 200 may be used to couple one portion of bodily tissue to another portion of bodily tissue.

The medical device 200 includes an elongate member 210, a suture 230, and a needle 240. The medical device 200 also includes a support or support member 260. In the illustrated embodiment, the medical device 200 includes a plurality of elongate members and sutures. In some embodiments, the elongate members and sutures are structurally and functionally similar. Only one of the elongate members and sutures of the device 200 will be described in detail.

The elongate member 210 has a first end portion 212 and second end portion 214. The elongate member 210 defines a lumen 216 that extends from the first end portion 212 to the second end portion 214. The elongate member 210 also defines a slot 218 that extends from the first end portion 212 to the second end portion 214. The slot 218 is in fluid communication with the lumen 216. In other words, the slot 218 is disposed adjacent to or leads to the lumen 216.

In the illustrated embodiment, the elongate member 210 includes a sidewall 219 that defines the lumen 216. The sidewall 219 also defines the slot 218.

The elongate member 210 can be of any shape or size. In the illustrated embodiment, the elongate member 210 is tubular with an outer surface that is generally smooth and round. As best illustrated in FIG. 6, the elongate member 210 (or the sidewall 219 of the elongate member 210) has a "C"-shaped cross-section. Specifically, the elongate member 210 (or the sidewall 219 of the elongate member 210) has a "C"-shaped cross-section along a cross-section that is perpendicular to a longitudinal axis of the elongate member 210.

As best illustrated in FIG. 5, in the illustrated embodiment, the elongate member 210 includes a tapered portion 223 or includes a tapered shape. In the illustrated embodiment, the first end portion 212 of the elongate member 210 has a size or diameter S1. The second end portion 214 of the elongate member 210 has a size or diameter S2 that is different and smaller than S1.

The suture 230 is configured to be tied to a bodily implant and bodily tissue to help secure the bodily implant within the body of the patient. The suture 230 can be formed or any type of biocompatible material. In some embodiments, the suture 230 is formed of a permanent material. In other embodiments, the suture 230 is formed of a bioresorbable material. In yet other embodiments, the suture 230 is formed of both permanent material and bioresorbably material.

As best illustrated in FIG. 8, the suture 230 is wrapped or wound around the elongate member 210 (such as the outer surface of the elongate member 210). In other words, the suture 230 extends around, traverses, or is otherwise disposed adjacent the outer surface 213 of the elongate member 210. In the illustrated embodiment, the suture 230 is wrapped or wound around the elongate member 210 more than once or a plurality of times (to form a plurality of suture loops). Additionally, in the illustrated embodiment, the suture 230 is wrapped or wound around the elongate member 210 such that a portion 232 of the suture 230 is disposed between the wrapped or wound portion 236 and the elongate member 210. Accordingly, in such an embodiment, as discussed in more detail below, when the first end portion 234 is passed through the wraps of the suture 230 (such as after being passed through the lumen 216 of the elongate member 210) and the first end portion 234 and the second end portion 238 of the suture are pulled, a knot will form in the suture 230.

In some embodiments, the suture 230 is wrapped or wound around the elongate member 210 in linearly (the winds or loops of the suture 230 are substantially parallel with each other). In other embodiments, the suture 230 is wrapped or wound around the elongate member 210 such that the suture 230 is crisscrossed (or the winds or loops of the suture 230 are twisted). In other embodiments, the suture 230 is wrapped or wound around the elongate member 210 such that the suture 230 is wrapped on itself (the winds or loops of the suture 230 are on top of each other). In some embodiments, the suture 230 is wrapped or wound around the elongate member 210 in one direction. In other embodiments, the suture 230 is wrapped or wound around the elongate member 210 in two directions (a first direction and a second opposite direction).

The needle 240 is coupled to the first end portion 234 of the suture 230. The needle 240 is configured to pierce bodily tissue and guide the suture 230 or a portion of the suture 230 through bodily tissue and/or a bodily implant. In some embodiments, the needle or needle member 240 includes a sharp or tissue piercing end portion. The needle 240 may be linear or may be curved or have a curved portion.

As illustrated in FIGS. 2, 6, and 7, the elongate member 210 includes a coupling portion 211. The coupling portion 211 is configured to removably retain the needle 240. For example, the coupling portion 211 is configured to retain the needle 240 while the device 200 is being inserted or removed from the body of the patient. The needle 240 can be removed from the coupling portion 211 and used in the procedure.

In the illustrated embodiment, the coupling portion 211 includes a groove 201 disposed within the lumen 216. Specifically, in the illustrated embodiment, the sidewall 219 defines the groove 201. The groove 201, as best illustrated in FIGS. 2 and 7, is configured to receive and retain the needle 240, for example, during the insertion of the medical device 200 into the body of the patient. FIG. 2 illustrates a needle 240 (in solid lines) coupled within the groove 201 and the needle 240 (in dashed lines) in a position in which it is uncoupled from the groove 201. As best illustrated in FIGS. 2 and 7, when a portion of the needle 240 is coupled to the groove 201, another portion of the needle is disposed within the slot 218 to help stabilize the needle 240. In other embodiments, the needle 240 or a portion of the needle is disposed away or apart from the slot 218 when the needle 240 is coupled to the groove 201.

In other embodiments, the coupling portion includes a lumen, a cavity, or another structure configured to removably retain the needle.

As illustrated in FIGS. 9, 10, and 11, the medical device 200 includes a support or support member 260. The support member 260 is configured to overlay or surround a portion of the elongate member 210 and the suture 230. In the illustrated embodiment, the support member 260 is configured to overlay or surround the plurality of elongate members and sutures. In some embodiments, the support member 260 is configured to help retain the suture 230 on or wound around the elongate member 210. For example, in some embodiments, the support member 260 is configured to be frictionally coupled to the elongate member 210 around an outer surface of the elongate member 210. In other embodiments, the support member 260 is coupled to the elongate member 210 via a different mechanism or member.

As best illustrated in FIG. 11, the support member 260 has a curved shape. More specifically, the support member 260 has a curved, rounded, or semi-circular cross-sectional shape. In some embodiments, the support member has a "C"-shaped cross-section.

The medical device 200 is configured to be inserted into the body of a patient and removed from the body of the patient via a trocar. As best illustrated in FIG. 10, in the illustrated embodiment, the support member 260 includes a tapered portion 203 or includes a tapered shape to help facilitate the insertion into and/or removal from the body of the patient. In the illustrated embodiment, the first end portion 205 of the support member 260 has a size or diameter S3. The second end portion 207 of the support member 260 has a size or diameter S4 that is different and smaller than S3.

In the illustrated embodiment, six separate elongate members and suture pairs are disposed within the support member 260. Any number of elongate member and suture pairs may be disposed within the support member 260. Each suture may be used for a different knot or different coupling of the implant to bodily tissue within the body of the patient. For example, in some embodiments, between 3 and 10 elongate member and suture pairs are disposed within the support member 260. In some embodiments, more than 10 elongate member and suture pairs are disposed within the support member 260.

In the illustrated embodiment, the medical device 200 includes a bias member 277. The bias member 277 is disposed within a lumen 209 defined by the support member 260. The bias member 277 is configured to apply pressure or bias the elongate member and suture pairs that are disposed within the support member 260. For example, when one of the elongate member and suture pairs are removed from the support member 260 (such as to tie a knot or form a coupling within the body of the patient), the bias member 277 is configured to advance the remainder of the elongate member and suture pairs within the support member 260. In some embodiments, the bias member 277 is a spring. In other embodiments, the bias member 277 is another device that is configured to apply pressure to the elongate member and suture pairs.

In use, the medical device 200 may be used to secure or help secure a bodily implant within a body of a patient. For example, in some embodiments, the medical device 200 may be used to knot or tie suture knots to help secure the implant within the body of the patient.

The medical device 200 may be inserted into a body of a patient. For example, in some embodiments, the medical device 200 is sized and shaped to be inserted into a body of a patient via a trocar. Specifically, in some embodiments, the medical device 200 is sized and shaped to be inserted into the body of the patient via a 10 mm-12 mm trocar. In other embodiments, the medical device 200 is sized and shaped to be inserted into the body via trocar that is smaller than 10 mm.

The medical device 200 may be disposed adjacent a bodily implant that has been placed or inserted into the body. The elongate member 210 and suture 230 may be removed or slid out from the support member 260. The needle 240 may be used to pass a portion of the suture 230 through the implant and through bodily tissue. For example, the needle 240 may be pressed or pushed against the implant and the bodily tissue to thread the suture 230 through the implant and through the bodily tissue. In some embodiments, tweezers or another medical device, such as graspers or needle drivers, is inserted into the body of the patient and used to press or push the needle 240 through the implant and/or bodily tissue.

The needle 240 may then be passed through the windings of the suture 230. For example, in some embodiments, the needle 240 and a portion of the suture 230 may be passed through the lumen defined by the elongate member 210 to extend or pass the needle 240 and a portion of the suture 230 through the windings of the suture (the portion of the suture 230 that is wound or wrapped around the elongate member 210).

The suture 230 may then be removed from the elongate member 210. For example, the suture 230 or the portion of the suture 230 that is wound around the elongate member 210 may be slid off of the elongate member to remove the suture from the elongate member 210. Additionally, in the illustrated embodiment, the portion of the suture that passes through the lumen 216 of the elongate member 210 may be removed from the elongate member 210 by passing such portion of the suture 230 through the slot 218. Accordingly, the suture 230 may be removed from the elongate member 210.

The end portions 234 and 238 of the suture 230 may then be pulled to cinch, secure or form the knot against the implant and the bodily tissue. The needle 240 may then be cut from the suture 230 to free the needle 240 from the suture 230. In the illustrated embodiment, the support member 260 defines a slot 279. The slot 279 is in communication with a cavity 281 defined by the support member 260. In some embodiments, after the needle 240 has been cut from the suture 230, the needle 240 may be disposed within the cavity 281 by inserting the needle 240 through the slot 279. Accordingly, in such embodiments, the needle 240 may be removed from the body of the patient with the support member 260.

In some embodiments, the elongate member 210 may be removed from the body of the patient. In other embodiments, the elongate member 210 may be formed of bioresorbable material and may be left within the body of the patient to be resorbed or absorbed by the body of the patient.

As more than one elongate member and suture pair are disposed within the support member 260, after the first suture 230 is removed from the elongate member 210 and a knot is formed, a second elongate member and suture pair may be removed from the support member 260 and the process may be repeated to form a second or additional knot to help secure the implant within the body of the patient.

Once all of the sutures have been placed (or all that are desired to be placed within the body of the patient), the support member 260 (and any needle disposed within the cavity of the support member 260) may then be removed from the body of the patient. In some embodiments, the support member 260 may be removed from the body of the patient via a trocar.

In the illustrated embodiment, the medical device 200 includes a retrieval member 299. The retrieval member 299 is configured to be grasped by the physician (for example, with tweezers or another medical device) and pulled to remove the medial device 200 from the body of the patient. In the illustrated embodiment, the retrieval member 299 is coupled to and extends from the support member 260. The retrieval member 299 includes or forms a loop 297 to facilitate the grasping of the retrieval member 299.

Figure 12:
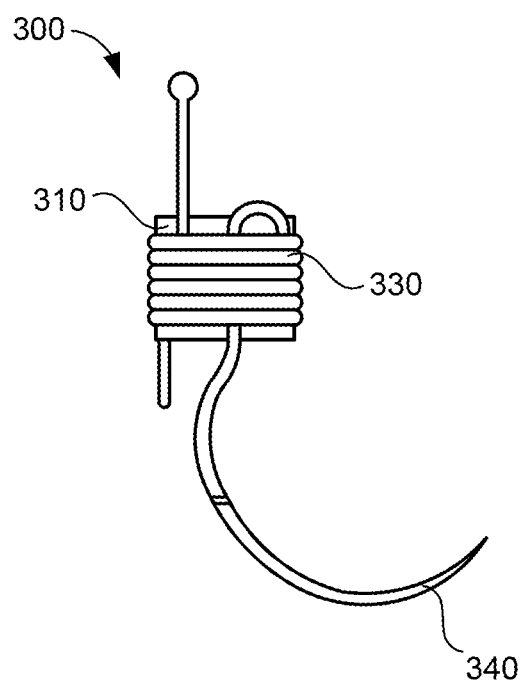
FIG. 12 is side view of an elongate member according to another embodiment.

FIG. 12 is a side view of an elongate member 310 and suture 330 of a medical device 300 according to an embodiment. The medical device 300 may be used to couple or attach a bodily implant within a body of a patient. For example, the medical device 300 may be used to couple or attach an implant within a pelvic region of a patient. For example, in some embodiments, the medical device 300 may be used in a sacrocolpopexy procedure to couple an implant to a vagina or tissue proximate a vagina of a patient. In other embodiments, the medical device 300 may be used to couple or attach different types of bodily implants into different locations within the body of the patient.

The medical device 300 includes an elongate member 310, a suture 330, and a needle 340. The elongate member 310 has a first end portion and second end portion. The elongate member 310 defines a lumen 316 that extends from the first end portion to the second end portion. The elongate member 310 also defines a slot 318 that extends from the first end portion to the second end portion. The slot 318 is in fluid communication with the lumen 316. In other words, the slot 318 is disposed adjacent to or leads to the lumen 316.

The medical device 300 may be inserted into a body of a patient. For example, the medical device 300 is sized and shaped to be inserted into a body of a patient via a trocar. Specifically, the medical device 300 is sized and shaped to be inserted into the body of the patient via a 10 mm-12 mm trocar. In other embodiments, the medical device 300 is sized and shaped to be inserted into the body via trocar that is smaller than 10 mm.

Figure 13:
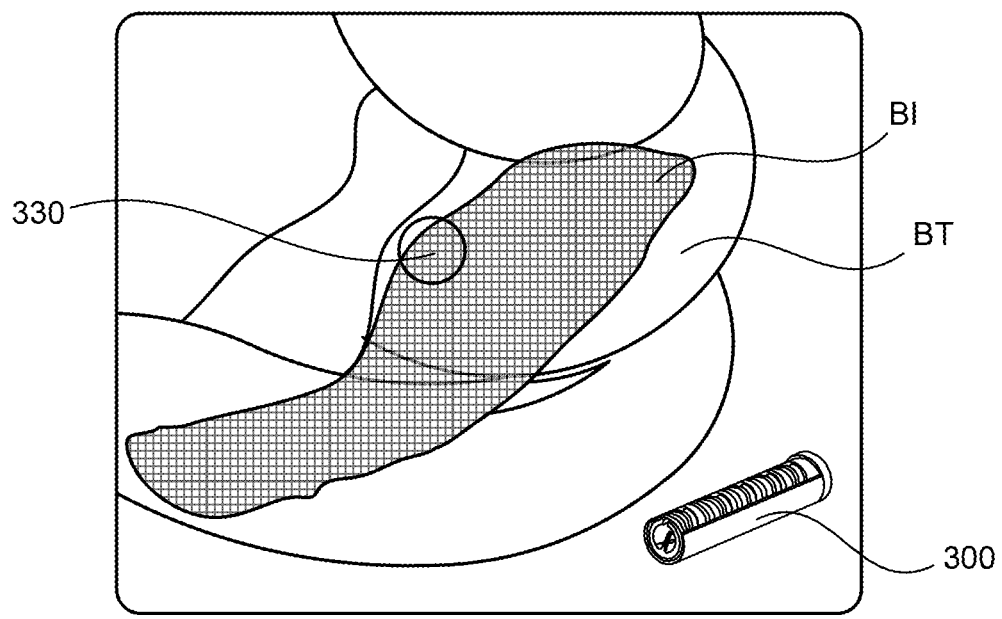
FIG. 13 is a schematic illustration of a medical implant and medical device disposed within a body of the patient.

As schematically illustrated in FIG. 13, the medical device 300 and a bodily implant is disposed within a body of a patient.

Figure 14:
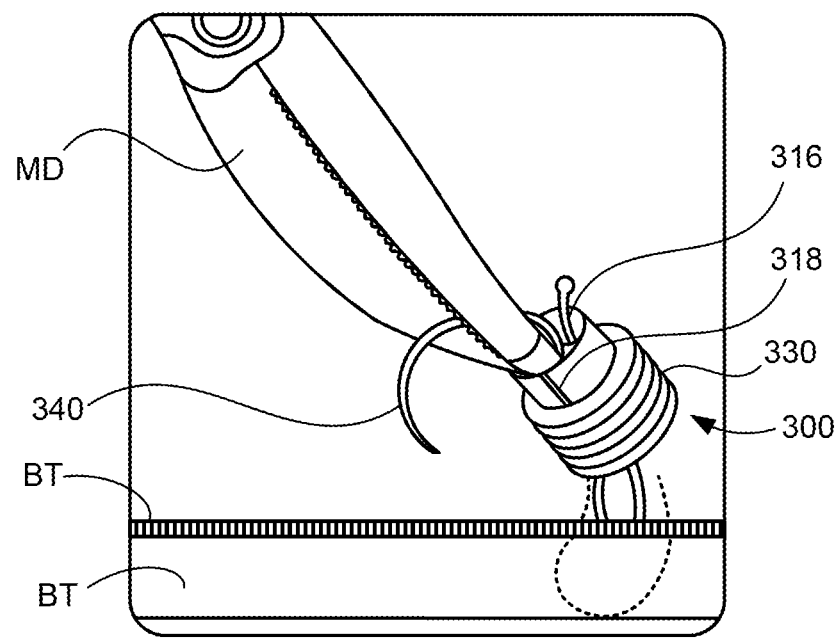
FIG. 14 is a schematic illustration of the medical device disposed within a body of a patient and in a first configuration.

As schematically illustrated in FIG. 14, the medical device 300 may be disposed adjacent the bodily implant within the body. The needle 340 may be used to pass a portion of the suture 330 through the bodily implant BI and through bodily tissue BT. For example, the needle 340 may be pressed or pushed against the implant BI and the bodily tissue BT to thread the suture 330 through the implant and through the bodily tissue. In the illustrated embodiment, tweezers or another medical device MD is inserted into the body of the patient and used to press or push the needle 330 through the implant and/or bodily tissue.

The needle 340 may then be passed through the windings of the suture 330. For example, in some embodiments, the needle 340 and a portion of the suture 330 may be passed through the lumen defined by the elongate member 310 to extend or pass the needle 340 and a portion of the suture 330 through the windings of the suture (the portion of the suture 330 that is wound or wrapped around the elongate member 310).

Figure 15:
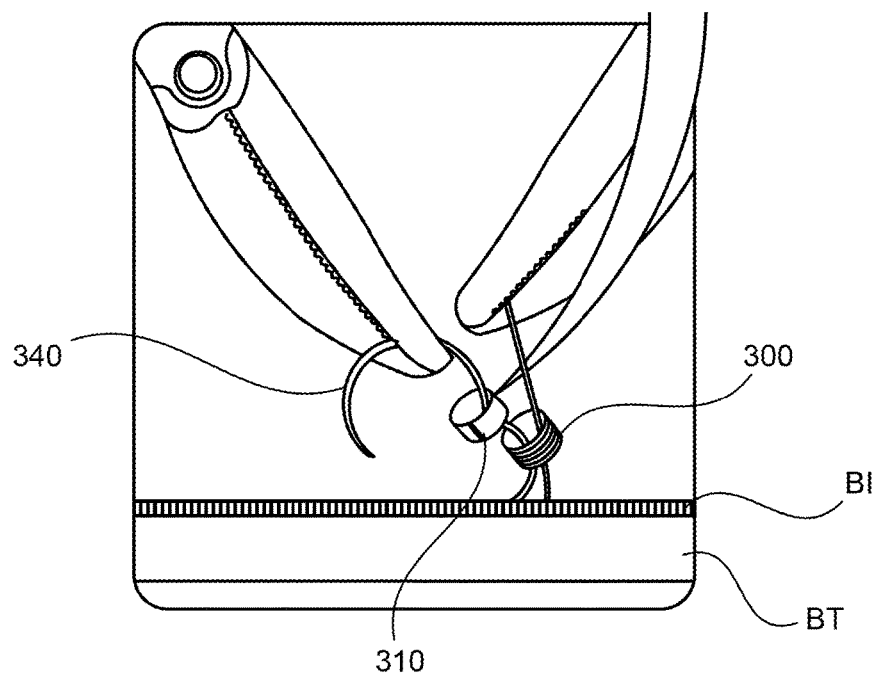
FIG. 15 is a schematic illustration of the medical device disposed within the body of the patient in a second configuration.

As schematically illustrated in FIG. 15, the suture 330 may then be removed from the elongate member 310. For example, the suture 330 or the portion of the suture 330 that is wound around the elongate member 310 may be slid off of the elongate member to remove the suture from the elongate member 310. Additionally, in the illustrated embodiment, the portion of the suture that passes through the lumen 316 of the elongate member 310 may be removed from the elongate member 310 by passing such portion of the suture 330 through the slot 318. Accordingly, the suture 330 may be removed from the elongate member 310.

Figure 16:
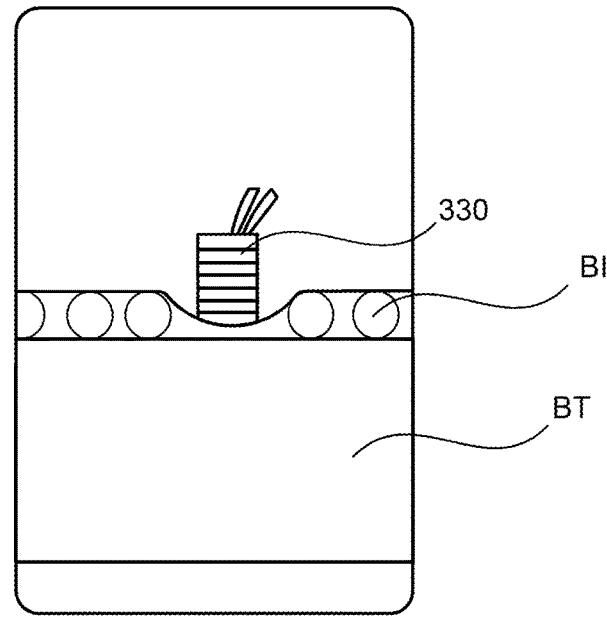
FIG. 16 is a schematic illustration of the medical device disposed within the body of the patient in a third configuration.
Figure 17:
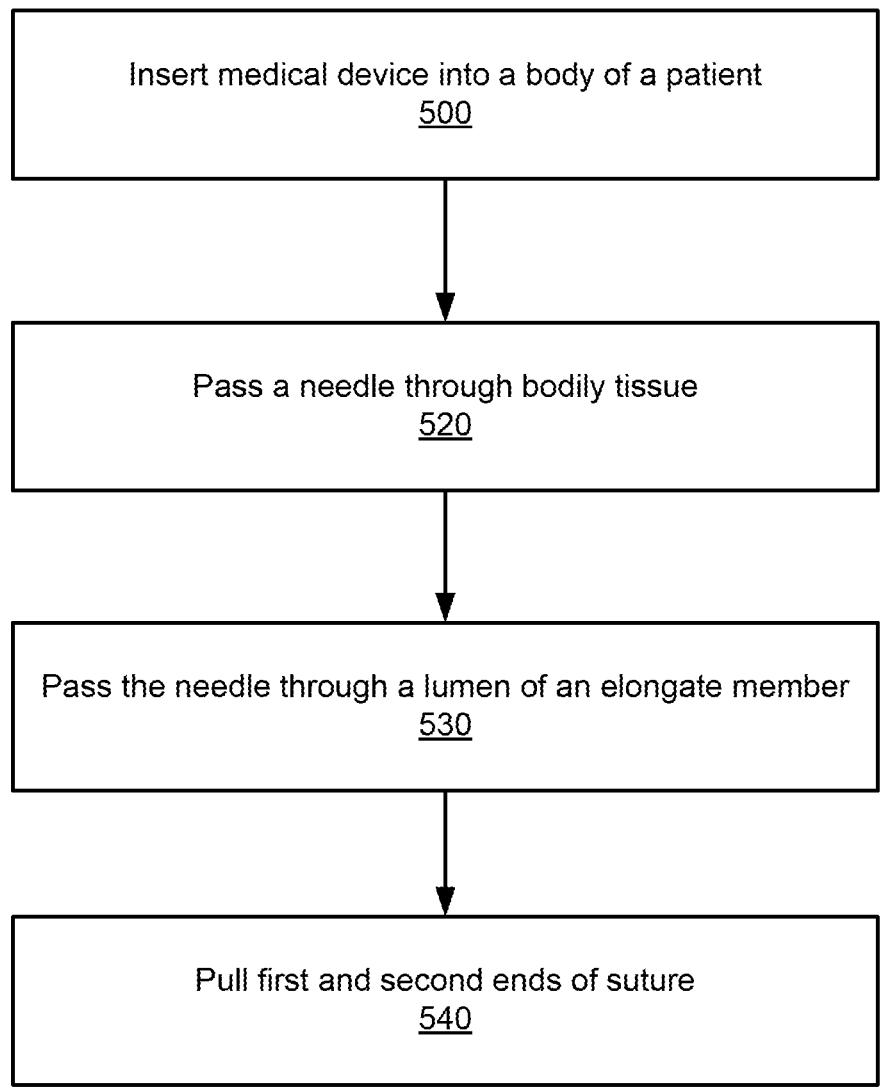
FIG. 17 is a flow chart of a method according to an embodiment.

The end portions of the suture 330 may then be pulled to cinch, secure or form the knot against the bodily implant BI and the bodily tissue BT. In some embodiments, two pairs of tweezers may be used to pull the end portions of the suture. The needle 340 may then be cut from the suture 330 to free the needle 340 from the suture 330 (as schematically illustrated in FIG. 16).

Accordingly, the bodily implant BI may be coupled to a portion of a body of a patient. In the illustrated embodiment, the bodily implant BI is a mesh material. In other embodiments, the bodily implant BI is of another type of material or form. In the illustrated embodiment, the bodily tissue BT is a vagina of a patient or bodily tissue disposed proximate a vagina of a patient. In other embodiments, the bodily tissue BT is another type of bodily tissue. In the illustrated embodiment, a plurality of knots or knotted sutures may be used to help couple the bodily implant BI to the bodily tissue BT.

Once all of the sutures have been placed (or all that are desired to be placed within the body of the patient), the support member of the device and the needle 340 may then be removed from the body of the patient.

FIG. 15 is a flow chart of a method 500 according to an embodiment. At 510, a medical device is placed within a body of the patient. The medical device includes an elongate member, a suture, and a needle. At 520, the needle, which is coupled to the suture, and a portion of the suture are passed through a bodily implant and bodily tissue. At 530, the needle and a portion of the suture is passed through a lumen defined by the elongate member. At 540, the first end portion and the second end portion of the suture are pulled to form a knot in the suture.

In some embodiments, the suture is removed from the elongate member by passing a portion of the suture through a slot defined by the elongate member. In some embodiments, the needle is cut from the suture and the needle and the elongate member are removed from the body of the patient.

In some embodiments, the device includes more than one suture and more than one needle. In such embodiments, each of the sutures may be placed within the body such that they form knots to help retain an bodily implant within the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A device, comprising:
an elongate member, the elongate member having a first end and a second end, the elongate member defining a lumen and a slot, the slot being in communication with the lumen, the lumen extending from the first end to the second end, the slot extending from the first end to the second end;
a suture, the suture being wrapped around the elongate member a plurality of times to form a plurality of suture loops, each suture loop being wrapped circumferentially around the elongate member; and
a needle, the needle being coupled to the suture.

2. The device of claim 1, wherein the first end of the elongate member has a first size, the second end of the elongate member has a second size, the first size being greater than the second size.

3. The device of claim 1, wherein the elongate member includes a tapered portion.

4. The device of claim 1, wherein the elongate member includes a coupling portion, the coupling portion being configured to removably couple the needle to the elongate member.

5. The device of claim 1, further comprising:
a support member, the support member being coupled to the elongate member and extending around at least a portion of the elongate member and the portion of the suture that is wrapped around the elongate member.

6. The device of claim 5, wherein the support member defines a cavity, the cavity being configured to receive the needle.

7. The device of claim 5, further comprising:
an extension member coupled to and extending from the elongate member.

8. The device of claim 5, further comprising:
an extension member coupled to and extending from the elongate member, the extension member having a loop portion.

9. The device of claim 5, wherein the support member defines a cavity and a slot in communication with the cavity, the slot being configured to receive the needle and the cavity being configured to house the needle.

10. A device, comprising:
an elongate member, the elongate member having a sidewall and having a first end and a second end, the sidewall of the elongate member having a substantially C-shaped cross-section, the sidewall defining a lumen and a slot, the slot being in communication with the lumen, the lumen extending from the first end to the second end, the slot extending from the first end to the second end;
an extension member coupled to and extending from the elongate member;
a suture, a portion of the suture being wrapped around the elongate member; and
a needle, the needle being coupled to the suture.

11. The device of claim 10, wherein the portion of the suture is wrapped around the elongate member a plurality of times.

12. The device of claim 10, further comprising:
a support member, the support member being coupled to the elongate member and extending around at least a portion of the elongate member and the portion of the suture that is wrapped around the elongate member.

13. The device of claim 12, wherein the support member defines a cavity, the cavity being configured to receive the needle.

14. The device of claim 10, wherein the elongate member includes a coupling portion, the coupling portion being configured to removably couple the needle to the elongate member.

15. A method, comprising:
inserting a medical device into a body of a patient, the medical device including
an elongate member, the elongate member having a first end and a second end defining a longitudinal axis, the elongate member defining a lumen and a slot, the slot being in communication with the lumen, the lumen extending from the first end to the second end, the slot extending from the first end to the second end,
a suture being wrapped around the elongate member a plurality of times to form a plurality of suture loops, each suture loop being wrapped circumferentially around the elongate member along the longitudinal axis, and
a needle coupled to the suture;
passing the needle through bodily tissue;
passing the needle through a lumen defined by the elongate member; and
pulling on a first end portion of the suture and a second end portion of the suture to form a knot in the suture.

16. The method of claim 15, further comprising:
removing a portion of the suture that is wound around the elongate member from the elongate member.

17. The method of claim 15, further comprising:
passing the needle through a bodily implant before the passing the needle through a lumen defined by the elongate member.

18. The method of claim 15, wherein the inserting the medical device into the body of the patient includes passing the medical device through a trocar.

19. The method of claim 15, further comprising:
removing the needle from the body of the patient.

* * * * *